United States Patent [19]

Knollenberg

[11] 4,027,162
[45] May 31, 1977

[54] METHOD AND APPARATUS FOR ORIENTING AND MEASURING FIBROUS PARTICLES

[75] Inventor: Robert G. Knollenberg, Boulder Heights, Colo.

[73] Assignee: Particle Measuring Systems, Inc., Boulder, Colo.

[22] Filed: Apr. 26, 1976

[21] Appl. No.: 680,011

[52] U.S. Cl. .............................. 250/345; 250/491; 250/492 R
[51] Int. Cl.² ......................................... G01J 1/00
[58] Field of Search ............... 73/432 PS; 250/574, 250/345, 492, 312; 356/102, 103, 104, 207, 208, 206

[56] References Cited

UNITED STATES PATENTS

| | | | |
|---|---|---|---|
| 2,873,644 | 2/1959 | Kremen et al. | 356/104 |
| 3,618,061 | 11/1971 | Livers | 356/208 |
| 3,692,412 | 9/1972 | Chubb | 356/103 |
| 3,705,771 | 12/1972 | Friedman | 356/104 |
| 3,835,315 | 9/1974 | Gravitt | 250/574 |
| 3,960,449 | 6/1976 | Carleton et al. | 250/574 |

*Primary Examiner*—Harold A. Dixon
*Attorney, Agent, or Firm*—O'Rourke, Harris & Hill

[57] ABSTRACT

Method and apparatus for orienting and measuring fibrous particles by conducting longitudinally oriented fibrous particles through a beam of radiation and measuring the radiation scattered in a direction aligned with the length of such particle and, independently, also measuring the amount of radiation scattered transverse to the length of the particle. Preferably, the measurements are accomplished utilizing a sensor having an inactive center portion substantially corresponding to the area of undisturbed beam of radiation, a first photosensitive area in a portion of the sensor aligned with the length of the particles, and a second, independent photosensitive area transverse to the length of the particle. Signals generated by the two photosensitive areas are added to determine the size of the particles, and the ratio between the signals is established to determine the aspect ratio of the particle. Preferably, the particles are aligned by conducting the particles entrained in a compressible fluid through a conduit of decreasing cross section whereby the varying flow rates across the cross section influence particles not aligned with the direction of flow. When the particles are aligned with the direction of flow, the particle is stably oriented.

13 Claims, 8 Drawing Figures

U.S. Patent    May 31, 1977    4,027,162
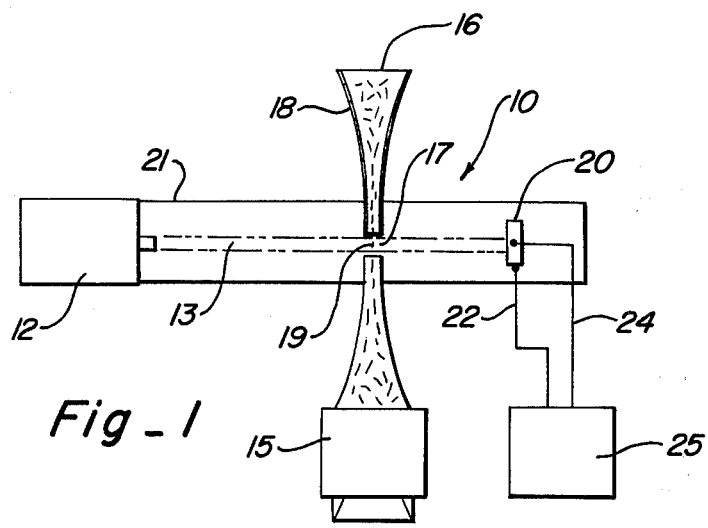
Fig_1
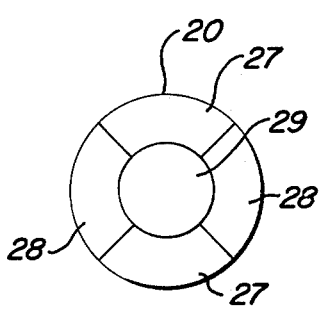
Fig_2
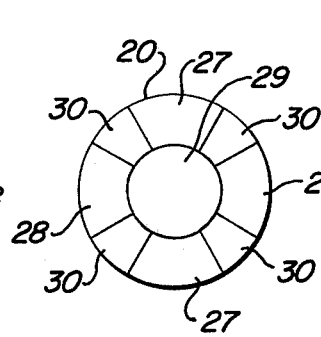
Fig_3
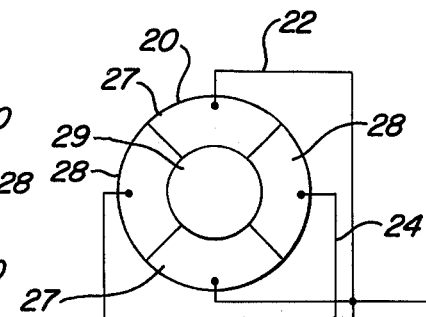
Fig_4
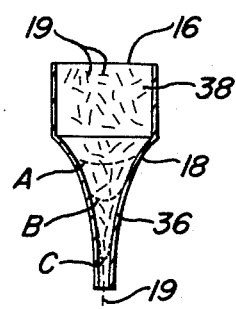
Fig_5
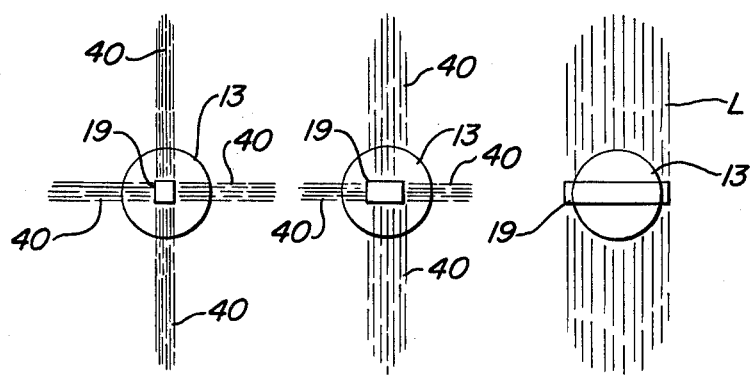
Fig_6    Fig_7    Fig_8

METHOD AND APPARATUS FOR ORIENTING AND MEASURING FIBROUS PARTICLES

BACKGROUND OF THE INVENTION

1. Field of the Invention

The present invention relates generally to method and apparatus for measuring fibrous paticles, and more particularly to a method and apparatus for measuring fibrous particles through asymmetric scattering of a radiation beam as a result of passing oriented fibers through the beam, and a preferred method and apparatus for providing orientation of the fibrous particles.

2. Description of the Prior Art

Measurement of particle characteristics as a function of the scattering of light is, per se, known. For instance, Freedman U.S. Pat. Nos. 3,705,711 and 3,785,735 issued Dec. 12, 1972 and Jan. 15, 1974, respectively, discloses the concept of utilizing fluid dynamics to narrow a sample liquid stream by enclosing it in a laminar flow stream. However, aspect ratio is not a concern of the Freedman patents. Accordingly, these prior patents are not pertinent to measurement of fibrous particles.

The Gravet U.S. Pat. No. 3,835,315, issued Sept. 10, 1974, discloses a concept of utilizing concentric, conical sheets of radiation to measure the size and non-spherical characteristic of particles. Eccentricity of particles is determined by the rather complicated and step wise utilization of polarized radiation.

SUMMARY OF THE INVENTION

The present invention, which provides a heretofore unavailable improvement over previous fibrous particle measuring devices and method, comprises a method and apparatus for, as a function of asymmetric scattering of light by oriented particles, providing signal outputs indicative of the size of a particle and the aspect ratio of the particle. The method and apparatus preferably employs a conduit of decreasing cross section to longitudinally orient the fibrous particles carried in a compressible fluid, means to conduct the oriented fibrous particles through a beam of radiation, and means to measure the scattering and direction thereof to provide the desired data.

Accordingly, an object of the present invention is to provide a new and improved method and apparatus for concurrently measuring the size and aspect ratio of fibrous particles.

Another object of the present invention is to provide a new and improved method and apparatus for longitudinally orienting fibrous particles.

Yet another object of the present invention is to provide a new and improved method and apparatus for utilizing asymmetric scattering of radiation to measure and characterize the size and aspect ratio of fibrous particles.

Still yet another object of the present invention is to provide a new and improved method and apparatus for continuous, high speed sampling and measuring of fibrous particles.

A further object of the present invention is to provide a method and apparatus for producing data indicative of the size and aspect ratio of fibrous particles, such data being in appropriate form for storage in a data recorder.

These and other objects and features of the present invention will become apparent from the following description.

BRIEF DESCRIPTION OF THE DRAWINGS

In the Drawing

FIG. 1 is a simplified representation of a fibrous particle measurement apparatus in accord with the present invention;

FIG. 2 is a front view of a sensor in accord with the present invention;

FIG. 3 is a front view of a preferred sensor in accord with the present invention;

FIG. 4 is a simplified representation of the sensor of FIG. 2 in conjunction with the typical associated readout circuitry;

FIG. 5 is a sectioned view of a particle orienter device in accordance with the instant invention;

FIG. 6 is a simplified representation of the scattering pattern of a particle of equal length and width in a beam of radiation;

FIG. 7 is a simplified representation of the scattering pattern of a particle having a somewhat greater length than width in a beam of radiation; and FIG. 8 is a simplified representation of the scattering pattern of a greatly elongated particle in a beam of radiation.

DETAILED DESCRIPTION OF THE INVENTION

Turning now to the drawings, wherein like components are designated by like reference numerals throughout the various figures, apparatus for measuring fibrous particles is illustrated in FIG. 1 and generally designated by reference numeral 10. As will be more fully described hereinafter, fibrous particle measuring apparatus 10 utilizes radiation source 12 to generate beam of radiation 13. Fluid pump 15 is connected to inlet 16 through gap 17 to particle orienter 18. Particle orienter 18 is thus positioned adjacent radiation beam 13 with particle orienter 18 positioned adjacent to and transverse to radiation beam 13. Accordingly, fluid pump 15 induces flow of a stream of particles 19 through radiation beam 13 at gap 17. Enclosure 21 is provided to protect the device and preclude disruptive air currents from influencing particles 19. Sensor 20 is positioned to intercept radiation beam 13 and is connected by signal conductors 22 and 24 to readout means 25.

The nature of sensor 20 will be more readily understood with reference to FIGS. 2 and 3. As shown in FIG. 2, sensor 20 is divided into three areas of significance. $X$-coordinate sensor areas 27 and $y$-coordinate sensor areas 28 are independently sensitive to scattered radiation to generate signals as a function of the radiation falling thereon. Center area 29, which preferably corresponds substantially to the area struck by undisturbed radiation beam 13, is essentially inactive.

A preferred embodiment of sensor 20 is illustrated in FIG. 3. Essentially, the embodiment of FIG. 3 is functionally identical to that of FIG. 2 with regard to $x$-coordinate sensor areas 27, $y$-coordinate sensor areas 28 and center area 29. However, between $x$-coordinate sensor areas 27 and $y$-coordinate sensor areas 28, inactive intermediate areas 30 are provided. Scattered radiation falling on inactive intermediate areas 30 can be associated with scattered radiation falling primarily either in $x$-coordinate sensor areas 27 or $y$-coordinate sensor areas 28. Thus, by effectively blanking out intermediate areas 30, sensor 20, as illustrated in FIG. 3, is more sensitive to the aspect ratio of particle 19 being measured.

The specific operation of sensor 20 will be more readily understood with reference to FIG. 4, whereat it is illustrated that x-coordinate sensor areas 27 are connected by signal conductors 22 to both a signal ratioing readout 32 and a signal adding readout 34 which constitutes a preferred readout 25, although, of course, either signal ratioing readout 32 or signal adding readout 34 provides worthwhile data. As will be discussed in more detail below, the ratio of the scattered radiation falling on x-coordinate sensor areas 27 relative the amount of scattered radiation falling on y-coordinate sensor areas 28 is a function of the aspect ratio of the particle 19 producing the radiation scattering. Accordingly, the ratio of signals from areas 27 relative to areas 28, as indicated or recorded on signal ratioing readout 32, is a function of the aspect ratio of a given particle 19, i.e., the particle length to width ratio. Also, the total amount of radiation falling on areas 27 and 28 is a function of the size of a given particle 19. Thus, signal adding readout 34, which adds the signals provided through signal conductor 22 and signal conductor 24, indicates or records a signal which is indicative of the overall size of a given particle.

The function of particle orienter 18 will be more readily understood with reference to FIG. 5. As illustrated, particle orienter 18 includes a throat section 36, Of decreasing cross section and, for purposes of illustration, an approach section 38 of constant cross section. Fluid flow through the throat section 38 is relatively slow with particles 19 being randomly oriented. However, as the fluid flow moves through throat section 36 of decreasing cross section, the average velocity of the fluid increases. Accordingly, as shown, the point rate of flow at points across the cross section of throat section 36 becomes markedly different, i.e., increase substantially from points adjacent the wall relative to points at the center portion as shown in the velocity profiles A, B, and C. As is well known, this is a result of drag upon a fluid induced by the wall and the fluid and accordingly moves more slowly adjacent the wall and more rapidly towards the center with the flow rate essentially defining a number of streamlines across the cross section. As this becomes more pronounced, a particle oriented transverse to the flow tends to align with the direction of flow. Once the particle is aligned with the direction of flow, it will lie substantially in a common signal streamline where the rotating torque is zero. Accordingly, particles 19 are oriented from a random distribution in approach section 38 to an orientation aligned with the direction of flow in throat section 36. Thus, as particles 19 exit throat section 36, and, as illustrated in FIG. 1, intersect radiation beam 13, particles 19 are aligned in a position transverse to the direction of radiation beam 13.

Finally, with reference to FIGS. 6 through 8, the illustrations show that the scattering pattern is quit sensitive to changes in the aspect ratio of a particle. For instance, in FIG. 6, particle 19 is of substantially equal length and width. Thus, when positioned in radiation beam 13, a scattering pattern 40 having substantially equal x and y axis scattering is established. However, as illustrated in FIG. 7, when the particle 19 is somewhat longer than wider, scattering pattern 40 is such that substantially more radiation is scattered in the x-coordinate domain than in the y-coordinate domain. Finally, as illustrated in FIG. 8, when the particle 19 extends entirely through radiation beam 13, i.e., functionally an infinite length relative to radiation beam 13, scattering pattern 40 is such that the scattered radiation is entirely in the x-coordinate domain.

Summarily, the present invention provides for concurrent determination of the size and aspect ratio of a fibrous particle. This is accomplished by orienting the particle relative to a beam of radiation and, while passing the particle through the beam of radiation, measuring the scattered radiation in the longitudinal direction of the particle and in the direction transverse to that direction. The total scattered radiation and the ratio of the radiation scattered in each direction, respectively, provides the desired determinations. On yet another level, the invention provides for a unique means for aligning fibrous particles by entraining the particles in a compressible fluid flow and conducting the fluid through a conduit of decreasing cross sectional area. This means of orientation is particularly advantageous in that the particles are aligned substantially with the direction of flow.

Although only limited embodiments of the present invention have been illustrated and described, it is anticipated that various changes and modifications will be apparent to those skilled in the art, and that such changes may be made without departing from the scope of the invention as defined by the following claims.

What is claimed is:

1. A method for measuring elongated, fibrous particles comprising:
   orienting the particle along a common axis with the longitudinal axis of the particles aligned with the common axis;
   sequentially passing the oriented particles transversly through a beam of radiation in a direction along the common axis;
   generating a first signal which is a function of the radiation scattered in a direction having a component substantially parallel to the longitudinal axis of the particle as the particle passes through the beam of radiation;
   generating a second signal which is a function of the radiation scattered in a direction having a component substantially transverse to the longitudinal axis of the particle and transverse to the beam of radiation as the particle passes through the beam of radiation; and
   determining the ratio of the two signals;
   whereby, the aspect ratio of the particle can be established as a function of the measured scattered radiation.

2. A method of measuring fibrous particles as set forth in claim 1 further comprising determining the sum of the two signals defining the measured amounts of scattered radiation to establish the size of the particle.

3. A method for measuring fibrous particles as set forth in claim 1 in which the particles are oriented by entraining the particles in a compressible fluid and flowing the fluid through a conduit of a cross sectional area decreasing in the direction of flow.

4. A method for measuring fibrous particles as set forth in claim 3 in which the flow of the fluid and entrained particles is induced by suction adjacent an outlet defined by the conduit of decreasing cross sectional area.

5. A method for measuring fibrous particles comprising;
   inducing flow of fibrous particles entrained in a compressible fluid;
   flowing the entrained particle and fluid through a conduit of decreasing cross sectional area to orient the particles into alignment with the direction of flow;
   passing the oriented fibers through a beam of radiation;
   measuring the radiation scattered by the passing of the particle through the beam of radiation in a direction having a component substantially parallel to the longitudinal axis of the particle;
   measuring the radiation scattered by the passing of the particle through the beam of radiation in a direction having a component substantially transverse to the longitudinal axis of the particle and to the beam of radiation;
   determining the ratio of the two measured amounts of scattered radiation; and
   determining the sums of the two measured amounts of scattered radiation.

6. Apparatus for measuring elongated fibrous particles comprising:
   means for providing a beam of radiation;
   means for inducing flow of the fibrous particles in a direction transverse to and intersecting the beam of radiation;
   means communicating with the flow inducing means and positioned adjacent the beam of radiation for orienting the fibrous particles into a common alignment for movement through the beam of radiation;
   first sensor means for measuring radiation scattered primarily in a direction having a component substantially parallel to the longitudinal alignment of the particles;
   second sensor means for measuring radiation scattered primarily in a direction having a component substantially transverse to the longitudinal alignment of the particles and also transverse to the beam of radiation; and
   means for determining the ratio of the measurement outputs of the first and second sensor means.

7. Apparatus for measuring fibrous particles as set forth in claim 6 in which the orientation means comprise a conduit of decreasing cross sectional area and defining the outlet, the conduit being with the outlet adjacent to the beam of radiation.

8. Apparatus for measuring fibrous particles as set forth in claim 7 in which the means for inducing flow of the fibrous particles comprise suction means positioned adjacent the beam of radiation opposite the outlet of the conduit.

9. Apparatus for measuring fibrous particles as set forth in claim 6 in which the first and second sensors are mounted on a common support with an inactive circular center section substantially aligned with the beam of radiation with the first sensor means being of at least one fan-shaped configuration extending from the inactive circular center section, and the second sensor means also being of at least one fan-shaped configuration extending from the inactive circular center means in a direction substantially transverse to that in which the first sensor means extends.

10. Apparatus for measuring fibrous particles as set forth in claim 9 in which inactive areas are provided on the support between the first and second sensor means.

11. Apparatus for measuring fibrous particles as set forth in claim 6 which further comprises means for providing a sum of the outputs from the first and second sensor means.

12. Apparatus for measuring elongated fibrous particles comprising:
   means for generating a defined beam of radiation;
   means for inducing flow of fibrous particles entrained in a compressible fluid, the flow being in a direction transverse to and intersecting the beam of radiation;
   a particle orienting conduit of decreasing cross sectional area having an outlet defined at the smaller portion of the cross sectional area positioned with the outlet adjacent the beam of radiation and communicating with the means for inducing flow;
   a sensor having a planar surface transverse to the axis of the beam of radiation, the sensor having an inactive central area substantially corresponding to the beam of radiation, a first radiation sensitive area extending on either side of the inactive central area in a direction substantially parallel to the longitudinal alignment of the particles passing through the beam of radiation, a second radiation sensitive area extending from either side of the inactive center portion in directions substantially transverse to the first radiation sensitive areas;
   means for determining the ratio of signal outputs from the first and second radiation sensitive areas; and
   connective means connecting the means for determining the ratio of each of the first and second radiation sensitive areas.

13. Apparatus for measuring fibrous particles as set forth in claim 12 in which inactive areas are provided between each of the photosensitive areas extending from the inactive central portion of the sensor.

* * * * *

UNITED STATES PATENT AND TRADEMARK OFFICE
CERTIFICATE OF CORRECTION

PATENT NO. : 4,027,162
DATED : May 31, 1977
INVENTOR(S) : Robert G. Knollenberg

It is certified that error appears in the above-identified patent and that said Letters Patent are hereby corrected as shown below:

Column 3, line 59, "quit" should be "quite"
Column 3, line 50, "signal" should be "single"
Column 6, line 48, "of each" should be "to each"

Signed and Sealed this twenty-third Day of August 1977

[SEAL]

Attest:

RUTH C. MASON
*Attesting Officer*

C. MARSHALL DANN
*Commissioner of Patents and Trademarks*